(12) United States Patent
Landenberger et al.

(10) Patent No.: US 11,836,949 B2
(45) Date of Patent: Dec. 5, 2023

(54) METHOD FOR EVALUATING A COLOR INDICATOR

(71) Applicant: TESTO SE & CO. KGAA, Lenzkirch (DE)

(72) Inventors: Benjamin Landenberger, Freiburg (DE); Janosch Kneer, Freiburg (DE); Martin Zubler, Lenzkirch (DE)

(73) Assignee: TESTO SE & CO. KGAA, Lenzkirch (DE)

( * ) Notice: Subject to any disclaimer, the term of this patent is extended or adjusted under 35 U.S.C. 154(b) by 536 days.

(21) Appl. No.: 17/008,770

(22) Filed: Sep. 1, 2020

(65) Prior Publication Data

US 2021/0065403 A1 Mar. 4, 2021

(30) Foreign Application Priority Data

Sep. 2, 2019 (DE) .......................... 102019123474.3

(51) Int. Cl.
| | |
|---|---|
| *G06T 7/90* | (2017.01) |
| *G06N 20/00* | (2019.01) |
| *G01N 21/78* | (2006.01) |
| *G01N 31/22* | (2006.01) |
| *G01N 33/03* | (2006.01) |
| *H04N 23/88* | (2023.01) |

(52) U.S. Cl.
CPC .............. *G06T 7/90* (2017.01); *G06N 20/00* (2019.01); *H04N 23/88* (2023.01); *G06T 2207/20081* (2013.01)

(58) Field of Classification Search
CPC . G06T 7/90; G06T 2207/20081; G06N 20/00; H04N 23/88; G01N 21/78; G01N 31/22; G01N 33/03
See application file for complete search history.

(56) References Cited

U.S. PATENT DOCUMENTS

| | | | | |
|---|---|---|---|---|
| 10,105,300 B2 * | 10/2018 | Urban | ...................... | A61K 8/42 |
| 11,287,387 B2 * | 3/2022 | Kelly | .................. | G01N 21/783 |

(Continued)

FOREIGN PATENT DOCUMENTS

| | | |
|---|---|---|
| DE | 60126002 T2 | 6/2007 |
| DE | 102016202428 A1 | 8/2017 |

(Continued)

OTHER PUBLICATIONS

Extended European Search Report dated Jan. 29, 2021 from corresponding European Registration No. 20193743.0.

*Primary Examiner* — Asghar H Bilgrami
(74) *Attorney, Agent, or Firm* — Grogan, Tuccillo & Vanderleeden, LLP

(57) ABSTRACT

A method for determining the measurement value of a measurement quantity of a substance using a color indicator, the color indicator having at least one indicator field having previously been brought into contact with the substance, is characterized in that the color indicator and a color reference are visually sensed, the color reference having at least two reference fields of different colors, that an intermediate value of the measurement quantity is obtained with computer assistance based on the captured color values of the reference fields and the indicator field, and that the measurement value of the substance is obtained from this intermediate value.

13 Claims, 3 Drawing Sheets

(56) References Cited

U.S. PATENT DOCUMENTS

| | | | |
|---|---|---|---|
| 2006/0092030 A1* | 5/2006 | Povenmire | G01W 1/00 |
| | | | 340/601 |
| 2013/0273528 A1 | 10/2013 | Ehrenkranz | |
| 2013/0303869 A1* | 11/2013 | Rebec | A61B 5/1459 |
| | | | 600/365 |
| 2014/0051173 A1 | 2/2014 | Barstis et al. | |
| 2015/0055134 A1* | 2/2015 | Papautsky | G01N 21/278 |
| | | | 356/402 |
| 2015/0211987 A1 | 7/2015 | Burg et al. | |
| 2015/0308961 A1 | 10/2015 | Burg et al. | |
| 2017/0184506 A1* | 6/2017 | Patel | G01N 21/78 |
| 2017/0350823 A1* | 12/2017 | Kelly | G01N 21/783 |
| 2018/0136140 A1* | 5/2018 | Brendsel | G06T 7/0012 |
| 2019/0391013 A1* | 12/2019 | Morgan, III | G01N 21/01 |

FOREIGN PATENT DOCUMENTS

| | | |
|---|---|---|
| EP | 0953149 B1 | 11/1999 |
| EP | 2453242 A1 | 5/2012 |
| EP | 3650843 A1 | 5/2020 |
| WO | 2013116831 | 8/2013 |
| WO | 2013116831 A1 | 8/2013 |
| WO | 2016102337 | 6/2016 |

* cited by examiner

METHOD FOR EVALUATING A COLOR INDICATOR

CROSS-REFERENCE TO RELATED APPLICATIONS

This application claims priority to German Patent Application Serial No. 10 2019 123 474.3, filed on Sep. 2, 2019, which is hereby incorporated by reference herein in its entirety.

FIELD OF THE INVENTION

The invention relates to a method for determining the measurement value of a measurement quantity of a substance using a color indicator, the color indicator having at least one indicator field that was previously brought into contact with the substance.

BACKGROUND OF THE INVENTION

Such a method may for example be applied in the examination of a liquid wherein a substance is maintained in an indicator field on a test strip or test carrier showing a color change depending on a characteristic of the liquid.

SUMMARY OF THE INVENTION

Such examination methods are known and are for example used for examining the amount of free fatty acids or of polar compounds in cooking oil. However, these types of color changes are also used in the examination of other substances and measurement values, for example the pH value of a liquid. Supplying the user with a color scale as color reference with which he can evaluate a color change or coloring of the indicator field has proven to be effective.

A disadvantage is, however, that such color changes occur gradually so that a precise categorizing of the degree of color change is difficult. Furthermore, the colors in the indicator field do not correspond exactly to the color scale which further complicates the matching to a measurement value.

The invention therefore has the object to allow a simpler and in particular much more precise determination of a measurement value.

According to the invention this object is solved by the method steps of claim 1.

The method according to the invention is therefore characterized in that the color indicator and a color reference are visually sensed, the color reference having at least two reference fields of different colors, that an intermediate value of the measurement quantity is obtained with computer assistance based on the captured color values of the reference fields and the indicator field, and that the measurement value of the substance is obtained from this intermediate value.

The visual sensing may occur using a conventional digital camera or a smart phone, for example.

Thus, the advantage here is that the indicator field color values no longer need to be visually sensed and compared to a color reference.

Rather, the indicator field color value is obtained from the image. Using the captured reference fields color values, this indicator field color value is assigned to an intermediate value using computer assistance. Preferably, the intermediate value includes the same physical dimensions as the measurement value to be determined. The measurement value is then obtained from the intermediate value using computer assistance.

It is particularly advantageous when the indicator fields and reference fields are detected automatically, for example by pattern or edge recognition or using a predetermined location in relation to a location reference. Such a location reference may for example be marked separately so that it may be clearly identified.

Dependent on the color indicator, the indicator fields take on different colors. Thus, the colors may gradually vary or take on discrete color values.

In one embodiment of the invention, two differently colored reference fields each define the end colors of a color scale. In this way a whole scale of the potential indicator fields colors can be defined by few reference fields. Preferably, the end colors are each associated with an end value of the color indicator measurement range. For a pH color indicator, the measurement range may for example be between a pH value of 1 to 10. Thus, the end colors may for example be blue for pH 10 and red for pH 1. In this way, intermediate values of the measurement range may be chosen from or associated with the color scale.

In one embodiment, it is convenient to obtain the intermediate value by interpolation of the indicator field color value within the color scale and the associated end values.

The color indicators are subject to a variety of variations, for example due to production and/or application, so that the obtained intermediate values are subject to large statistical variation. In a particularly advantageous embodiment, obtaining the intermediate value and/or the measurement value from the intermediate value occurs using statistical processes and/or by artificial intelligence. In this way a statistical adaptation may occur by averaging over many individual measurements so that a more precise measurement value is obtained. In particular, in using artificial intelligence (AI), a significant improvement of the measurement accuracy is possible.

Artificial intelligence may receive the color value and/or intermediate value of each indicator field and the color value of each reference field as input and may produce the measurement value of the substance as output. In this way, many environmental influences may contribute to obtaining the measurement value. Artificial intelligence is therefore only applicable for exactly one combination of color indicator and color reference. This means that for a color indicator having another measurement quantity and other color values individual artificial intelligence must be trained.

In an advantageous development, each obtained measurement value may be used for further training artificial intelligence.

For improving the determination of the color values, it may be advantageous when automatic color balance, in particular white balance, is carried out. The color balance may for example be carried out via inner camera logic during or after the image capture.

In an advantageous embodiment, the color reference has at least one color matching field serving as basis for the color matching. This color balance field may for example be white for white balance or gray for gray balance. The color balance may for example occur before the color values of the indicator fields and the reference fields are determined.

However, it is also possible for the color balance fields color values to serve as additional input to the artificial intelligence. In this way, the automatic color balance occurs via artificial intelligence.

In principle it is possible to sense the color indicator and the color reference in separate images. However, capture parameters such as camera pose, distance to the object, angle to the object, focal length, aperture, exposure time, ISO sensitivity, lighting etc. influence obtaining the color values. To keep these capture parameters the same it is convenient for the visual sensing of the color indicators and the color reference to occur simultaneously, in particular in one image. Thus, a variation of the capture parameters mentioned above is minimized or excluded, so that obtaining the color values can occur more precisely.

To achieve a higher accuracy during evaluation it is advantageous for the color indicator to have more than one indicator field. In this way manufacturing deviations in the indicator field may for example contribute to obtaining the measurement value.

It can thus be convenient if the color indicator has at least two, in particular four, indicator fields. These indicator fields may be identical, so that there is multiple redundant information available for evaluation and a more accurate result can be achieved.

In an embodiment of the invention the indicator fields include different sensitivities to the substance to be measured. Thus, the individual indicator fields change their color for different measurement values so that the color indicator receives a spatial dimension, which can result in an additional improvement to accuracy.

In an advantageous embodiment the color reference has more than one reference field for each end color. These may for example be spaced apart from one another according to the indicator fields on the color indicator. In this way differences in illumination of the indicator fields within the image and for example geometric distortion may be accommodated and compensated.

It is particularly convenient for the multiple reference fields of an end color to each have identical colors. In particular it is convenient, if for each end color two reference fields are present, that are spaced apart from one another and/or alternately arranged. Using an alternate arrangement may result in a better distribution of the reference fields so that deviations in the image may be compensated, as described above.

A color indicator is usually formed to be submerged in a liquid or to be wetted with a liquid. Thereby, depending on the capture pose, reflections can emerge that in the worst case complicate or render impossible an evaluation of the color of an indicator field or a reference field.

In one embodiment the color indicator is therefore formed such that the substance to be measured is bound such that no reflections can arise from ambient light. To achieve this, a base carrier of the color indicator may be absorbent or may have a rough surface.

In one embodiment, means for detecting interfering reflections may be present so that a warning can be emitted, for example. Such means may for example already detect reflections before the image capture and may notify the user so that the camera pose and/or the lighting may be changed.

It may also be envisaged to calculate reflections out of an existing image via respective image processing algorithms, which may however impact accuracy.

In principle it is possible that the color indicator and the color reference are formed integrally or in multiple parts. It is advantageous if the color reference is formed separately as it can then be reused multiple times.

In a convenient embodiment the size and spacing of the reference fields are matched to the size and spacings of the indicator field respectively, in particular wherein the distances are identical so that the reference fields can each be placed next to an indicator field. Thereby the accuracy of the sensed color value may be improved as the color values may have a lesser deviation based on the locally similar lighting.

The invention further comprises a device for determining the measuring value of a substance characteristic using a color indicator. According to the invention, this device is characterized in that the device has an imaging unit for visual sensing of the color indicator and a color reference, and an evaluation unit for obtaining an intermediate value with computer assistance using the captured color values of the color reference fields and an indicator field of the color indicator, and for obtaining the measurement value of the substance from this immediate value.

Especially advantageously, the device is formed for performing a method according to the invention.

The device may be formed as a particularly adapted measuring apparatus. It is however particularly advantageous, if the device is a smart phone, a tablet or a notebook, in which the evaluation unit is formed by a software program or an app. Smart phones are very common and usually include an imaging unit, so that obtaining a measuring value according to the invention is simple and cheap to execute. The other advantage is that updates and/or improvements to obtaining the measuring value can be implemented anytime by a software update.

The invention is further discussed below according to an exemplary embodiment in relation to the drawings attached.

BRIEF DESCRIPTION OF THE DRAWINGS

The following show.

DETAILED DESCRIPTION OF THE DRAWINGS

Figure 1:
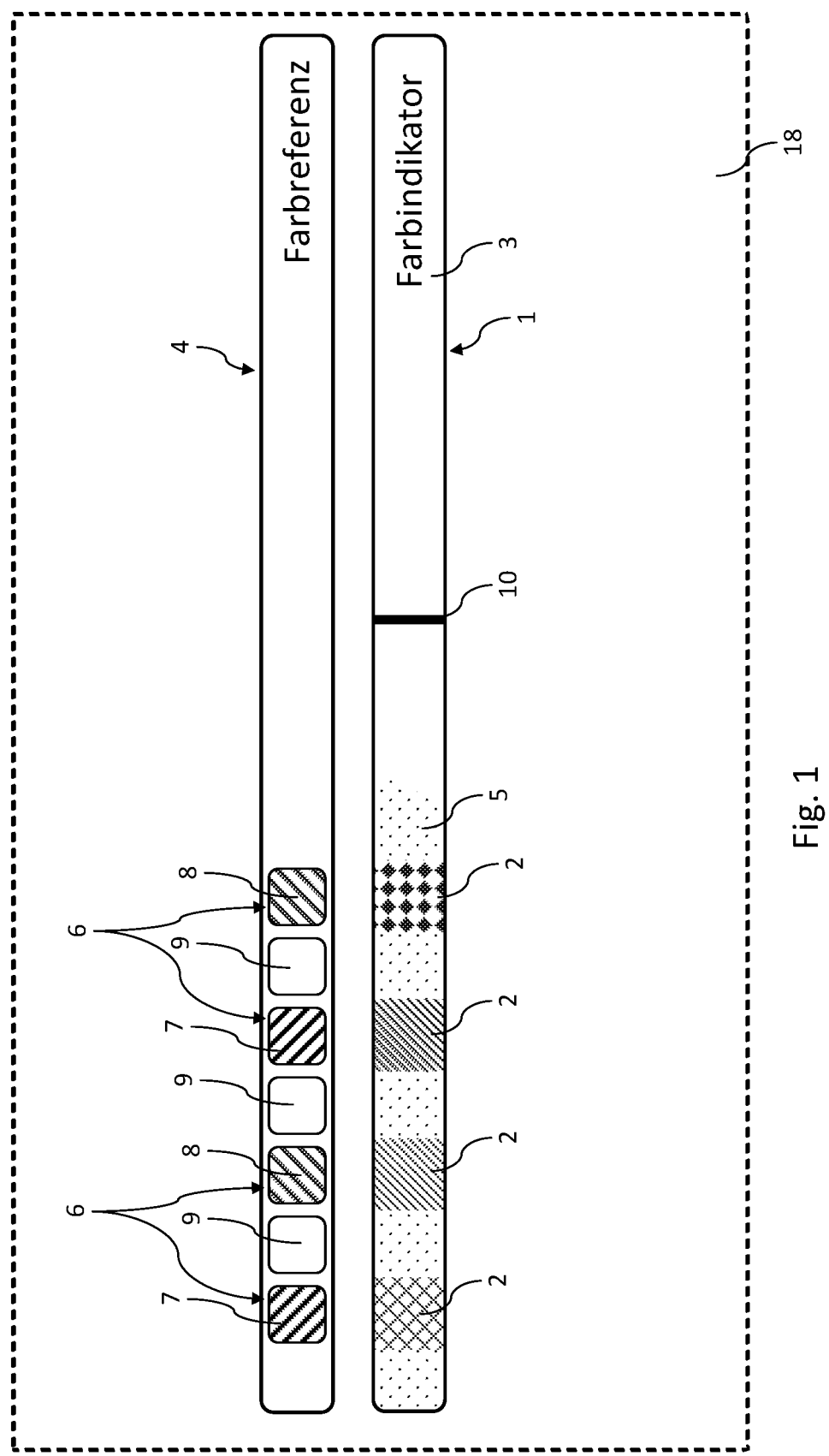
FIG. 1: a color indicator and a color reference in the form of test strips.

FIG. 1 shows a color indicator 1 for submerging in a liquid. Such a color indicator 1 may for example be employed for determining the pH value or other measurement quantities.

For example, a color indicator 1 for determining the free fatty acids in cooking oil is shown. Such a color indicator is for example available as a test strip from 3M™ under the name LRSM 200. The color indicator 1 includes four indicator fields 2 that are arranged equidistantly spaced apart from one another on a base carrier 3.

The indicator field 2 includes different sensibilies with this color indicator 1 so that a specific measurement value may be determined by the number of indicator fields 2 with color change. However, the color change occurs gradually.

The color indicator 1 includes a marking 10 showing a maximal submersion depth.

FIG. 1 further shows a color reference 4 that is also arranged on a strip-shaped base carrier 3. In the example the color reference 4 has four reference fields 6. Two of the reference fields 6 include a first end color 7 and the other two reference fields 6 include a second end color 8. The reference fields 6 with the two end colors are disposed alternately on the base carrier 3.

In the example, a white color balance field 9 is arranged between each of two reference fields 6 and may be used for an automatic white balance of an image. In the example, the color balance fields 9 include the same dimensions as the reference fields 6.

In particular the reference fields 6 include the same distances from each other as the indicator fields 2 so that a reference field 6 can each be arranged next to an indicator field 2, as shown in FIG. 1. Thereby color deviations based on irregular lighting may be reduced and thus the color assignment may be improved. The color reference may however be placed in a different location.

Figure 2:
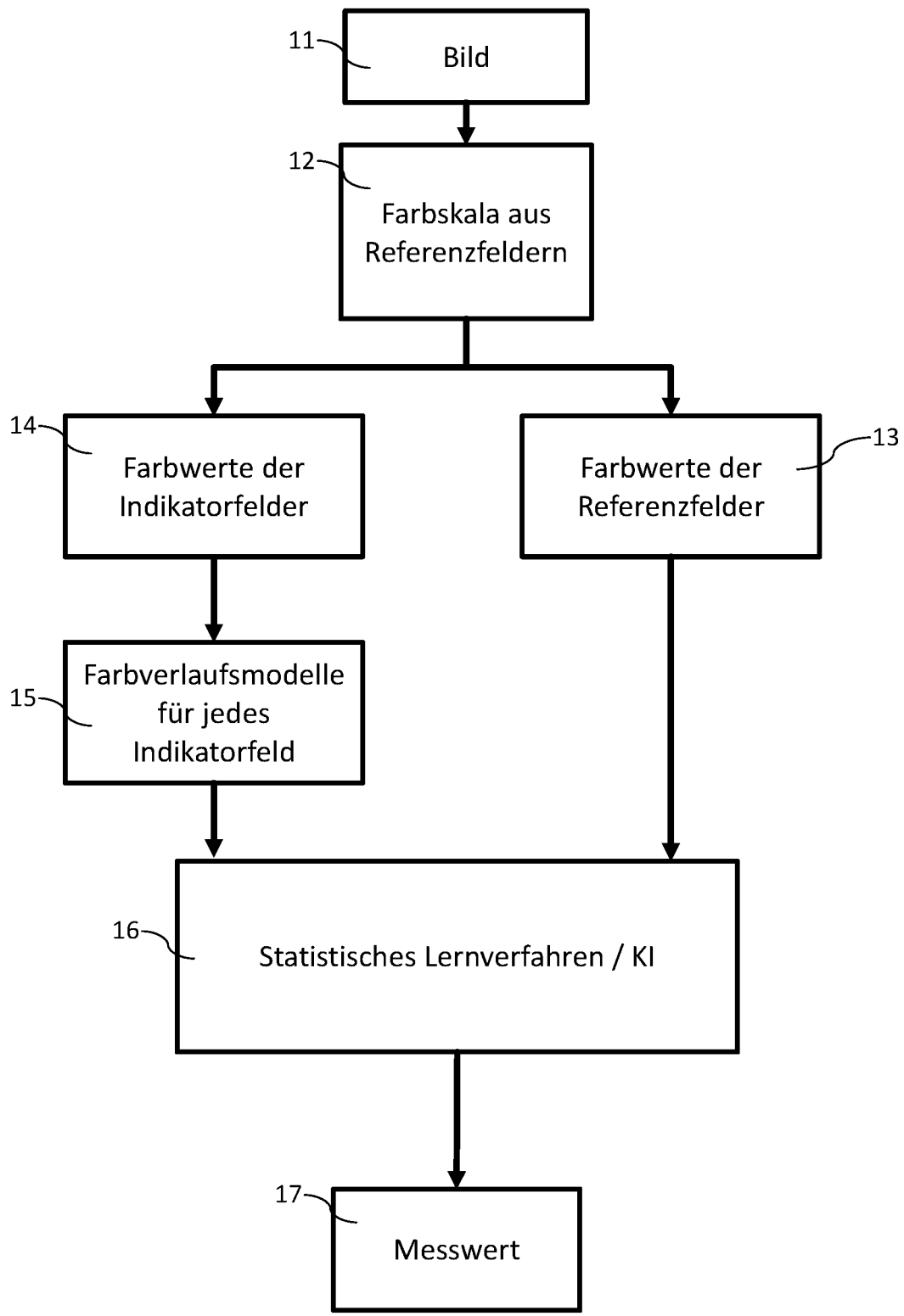
FIG. 2: a flow chart of a method according to the invention.
Figure 3:
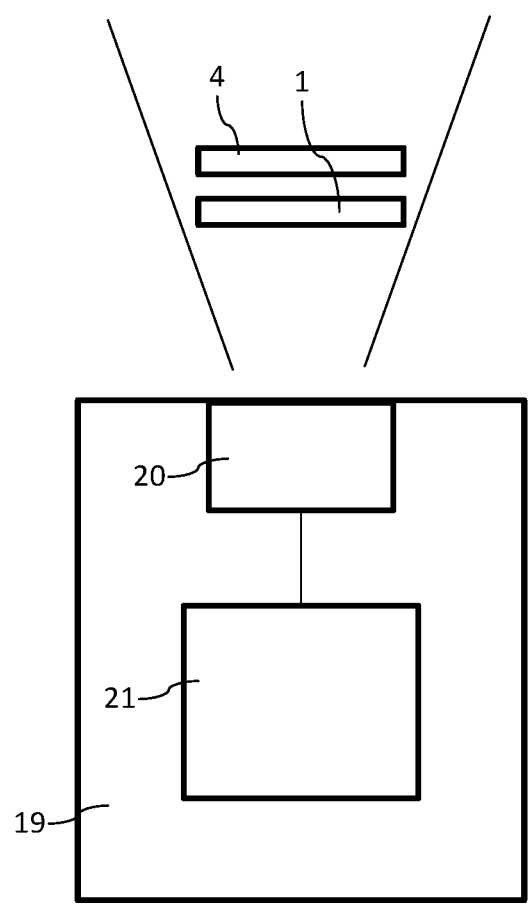
FIG. 3: a device according to the invention.

FIG. 2 shows a flow chart of an advantageous method according to the invention. In the example the content of free fatty acids in a frying or cooking oil of a deep fat fryer is to be determined. For this purpose, the LRSM 200 test strips described above are used as color indicator. The method may also be applied without change for determining other measurement quantities using different color indicators.

The color indicator 1 is first submerged to the marking 10 into the liquid to be tested, in the example the frying oil, such that all indicator fields 2 are wetted with frying oil 5.

In an imaging step 11 the color indicator 1 and a color reference 4 are sensed visually. Preferably the color indicator 1 and the color reference 4 may be sensed simultaneously in one image 18.

Therefore, the color indicator 1 and the color reference 4 may be placed next to each other on one surface, such as for example shown in FIG. 1. This has the advantage that all capturing parameters, such as the camera perspective and the lighting, for the color indicator 1 and the color reference 4 are identical, so that potentially interfering influences have a lesser relevance or can be calculated out.

Preferably the color reference 4 is adapted to the color indicator 1 such that the reference fields 6 have about the same dimensions and the same spacings as the indicator fields 2 of the color indicator 1.

However, it is also possible to separately capture the color indicator 1 and the color indicator 4, whereby the advantages mentioned above may not be present.

It is particularly convenient, if the image is sensed digitally, for example using a smart phone camera, or is at least provided to the method in digital form.

The method according to the invention may be formed in a separate apparatus or as an application program for carrying out on a mobile apparatus, particularly a smart phone or a tablet computer.

In a color scale step 12, a color scale is obtained from the reference fields 6. The color scale is thus defined by the first end color 7 and the second end color 8. Intermediate color values of the color scale are thus determined by color interpolation. Thereby different color models may be used wherein the selection of the color model may be dependent on the type of the color indicators.

Depending on the type of color indicator, the color scale may also be defined by more than two end colors, particularly wherein one or more intermediate colors are defined. The number of necessary reference fields is thereby potentially raised.

In color balance step 13, the color values of the color balance fields 9 are obtained. The color values may therefore be picked out from the digital image 18 in a usual format, for instance as RGB or HSV values.

The color balance fields 9 preferably each have the same color and serve to color balance the captured image 18. The color balance fields 9 may for example be white for an automatic white balance or gray for a gray balance. There may however also be white and gray color balance fields 9, so that a double color balance may be performed. A colored color balance field may also be present, for example in one color that is complementary to the two end colors, whereby an exact color balance is also possible. Through the spaced arrangement of multiple color balance fields 9 a balance of an uneven illumination of the image that may arise through different spacings in an oblique image capture, for example, is possible.

In an indicator step 14 the indicator fields 2 color values are obtained. The color values are conveniently obtained in the same format as the color balance fields 9 color values.

For automatic obtaining of the indicator fields 2 color values, the reference fields 6 and the color balance fields 9, a method for pattern detection, edge and/or corner detection and another known method for object detection may be used. The advantage is that the color indicator 1 and the color reference 4 may be sensed visually in almost any location and arrangement to one another. Thereby the application is very easy and less error-prone.

However, a location reference may be present on the color indicator 1 and/or the color reference 4, the location of which in relation to the other fields is known. Such a location reference may for example be a special symbol or for instance a QR code.

It is also possible that the color reference 4 is arranged in a defined location relative to the color indicator 1. The color reference 4 may for example have a recess to insert the color indicator 1.

In a model step 15, an intermediate value is determined for each indicator field 2 based on the color value and a color progression model associated with the indicator field 2. The intermediate value may already include the physical dimension of the measurement value to be determined.

These intermediate values are subject to a large statistical deviation. In particular because the sensitivities of the individual indicator fields cannot be reproduced exactly and because the color changes only occur gradually.

Thus, analytically obtaining a measurement value is hardly possible. Thus, a measurement value is obtained from the initial data based on artificial intelligence (AI) in an evaluation step 16.

The AI is based on a statistical machine learning system that is trained via a plurality of single measurements. In particular, the AI includes all obtained color values and intermediate values as input parameters. Accordingly, such an AI is only formed for evaluation of a specific color indicator together with a color reference.

Other color indicators with a different amount of indicator fields each require their own trained AI.

It may be convenient to use each performed measurement operation to further train the AI. Therefore, it may be advantageous, if the AI is for example formed on a central server as web service, so that all apps benefit equally from the continuing improvement.

What is claimed is:

1. A method for determining the measurement value of a measurement quantity of a substance using a color indicator, the color indicator having at least one indicator field having previously been brought into contact with the substance, wherein the color indicator is a test strip with at least one indicator field, wherein the color indicator and a color reference are visually sensed, the color reference having at least two reference fields of different colors, that an intermediate value of the measurement quantity is obtained with computer assistance based on the captured color values of the reference fields and the indicator field, and that the measurement value of the substance is obtained from this intermediate value;

wherein the intermediate value is obtained by interpolation of the indicator field color value within the color scale and the associated end value.

2. The method of claim 1, wherein two reference fields of different colors each define the end colors of a color scale, and the end colors are each associated with an end value of the color indicator measuring range.

3. The method of claim 1, wherein obtaining the measurement value from the intermediate value occurs using statistic processes and/or by artificial intelligence.

4. The method of claim 3, wherein the artificial intelligence receives the color value and/ or the intermediate value of each indicator field and the color of each reference field as input and produces the substance measurement value as output.

5. The method of claim 1, wherein an automatic color balance, specifically white balance, is carried out, the color reference in particular having at least one color balance field, and/ or that the color values of the color balance fields serve as further inputs of the artificial intelligence.

6. The method of claim 1, wherein the visual sensing of the color indicator and the color reference occurs simultaneously, in particular in one image.

7. The method of claim 1, wherein the color indicator has more than one indicator field, in particular four indicator fields, the indicator fieldsin particular having different sensitivities to the substance to be measured.

8. The method of claim 1, wherein the color reference has more than one reference field for each end color, the reference fields of one end color each having identical colors, in particular wherein for each end color two reference fields spaced apart from one another and alternately arranged are present.

9. The method of claim 1, wherein the color indicator is formed such that the substance to be measured is bound such that no reflections can arise from surrounding light and/ or that means to detect interfering reflections are present so that a warning may be emitted.

10. The method of claim 1, wherein the color indicator and the color reference are formed integrally or in multiple parts and/ or that the size and spacing of the reference fields match the size and the spacings of the indicator fields, in particular, the spacings being identical so that the reference fields can each be placed next to an indicator field.

11. A device for determining the measurement value of a characteristic of a substance using a color indicator wherein the device has an imaging device for visual sensing of the color indicators and a color reference, and an evaluation unit for obtaining an intermediate value with computer assistance using the captured color values of the color reference fields and an indicator field of the color indicator, and for obtaining the measurement value of the substance from this intermediate value, wherein the color indicator is a test strip with at least one indicator field;

wherein the intermediate value is obtained by interpolation of an indicator field color value within a color scale and an associated end value.

12. The device of claim 11, wherein the device is formed for performing the method of claim 1.

13. The device of claim 11, wherein the device is a smart phone, a tablet or a notebook, in which the evaluation unit is formed by a software program or an app.

* * * * *